United States Patent [19]

Kiehs et al.

[11] 4,042,628

[45] Aug. 16, 1977

[54] 2,6-DINITRO-4-TRIFLUOROMETHYLANILINES

[75] Inventors: Karl Kiehs; Karl-Heinz Koenig, both of Ludwigshafen; Adolf Fischer, Mutterstadt, all of Germany

[73] Assignee: Badische Anilin- & Soda-Fabrik Aktiengesellschaft, Ludwigshafen (Rhine), Germany

[21] Appl. No.: 560,122

[22] Filed: Mar. 20, 1975

Related U.S. Application Data

[63] Continuation of Ser. No. 174,158, Aug. 23, 1971, abandoned, and a continuation-in-part of Ser. No. 784,247, Dec. 16, 1968, Pat. No. 3,681,425.

[30] Foreign Application Priority Data

Dec. 21, 1967 Germany .............................. 1643719

[51] Int. Cl.$^2$ ...................... C07C 87/62; C07C 91/06; C07C 93/14; A01N 9/20

[52] U.S. Cl. ..................................... 260/577; 71/105; 71/121; 260/465 E; 260/573

[58] Field of Search ................... 260/577, 573; 71/121

[56] References Cited

U.S. PATENT DOCUMENTS

| | | | |
|---|---|---|---|
| 3,849,107 | 11/1974 | Fischer | 71/92 |
| 3,966,816 | 6/1976 | Woods et al. | 260/573 |
| 3,968,138 | 7/1976 | Hunter et al. | 260/465 E |
| 3,989,508 | 11/1976 | Fischer | 71/120 |

*Primary Examiner*—Daniel E. Wyman
*Assistant Examiner*—John J. Doll
*Attorney, Agent, or Firm*—Keil, Thompson & Shurtleff

[57] ABSTRACT

2,6-Dinitro-4-trifluoromethylanilines which are N,N-disubstituted by lower chloroalkyl and by lower alkyl, allyl, lower alkoxyalkyl or lower hydroxyalkyl; and herbicide uses thereof.

2 Claims, No Drawings

2,6-DINITRO-4-TRIFLUOROMETHYL-ANILINES

This application is a continuation of our application Ser. No. 174,158, filed Aug. 23, 1971, now abandoned, and a continuationin-part of our application Ser. No. 784,247, filed Dec. 16, 1968, now U.S. Pat. No. 3,681,425.

The present invention relates to new and valuable substituted dinitroanilines and a process for controlling the growth of unwanted plants with these compounds.

It is known to use N,N-dipropyl-4-trifluoromethyl-2,6-dinitroaniline for controlling the growth of unwanted plants, especially in cotton.

An object of the invention is new and valuable substituted dinitroanilines. More particularly an object of the invention is new and valuable 2,6-dinitroanilines. Yet another object of the invention is a process for controlling the growth of unwanted plants without damaging crop plants.

These and other objects of the invention are achieved by substituted dinitroanilines having the formula

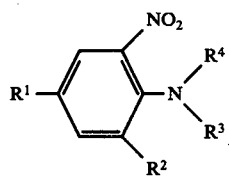

in which $R^1$ denotes trifluoromethyl, $R^2$ denotes nitro, $R^3$ denotes lower chloroalkyl or lower cyanolalkyl and $R^4$ denotes lower alkyl, allyl, lower chloroalkyl or lower cyanoalkyl. These substituted dinitroanilines have good herbicidal action and, when compared with active ingredients of similar constitution, have superior plant compatibility.

The new compounds may be applied as herbicides as solutions, emulsions, suspensions or dusts. The form of application depends entirely on the purpose for which the agents are being used; in any case it should ensure a fine distribution of the active ingredient.

For the preparation of solutions to be sprayed direct, mineral oil fractions with medium to high boiling points, such as kerosine or diesel oil, coal tar oils and oils of vegetable or animal origin, cyclic hydrocarbons, such as tetrahydronaphthalene, and alkylated naphthalenes are suitable.

Aqueous formulations may be prepared from emulsion concentrates, pastes or wettable powders by adding water. To prepare emulsions the ingredients as such or dissolved in a solvent may be homogenized in water by means of wetting or dispersing agents, e.g. a polyethylene oxide adduct. Concentrates which are suitable for dilution with water may be prepared from active ingredient, emulsifying or dispersing agent and possibly solvent.

Dusts may be prepared by mixing or grinding the active ingredients with a solid carrier, e.g. diatomaceous earth or fertilizers.

The new compound may be prepared for example by reaction of substituted dinitrochlorobenzenes with substituted amines. They are crystalline or non-distillable oils.

The following Examples illustrate the preparation of specific compounds according to this invention.

EXAMPLE 1

Preparation of N-chloroethyl-N-allyl-2,6-dinitro-4-trifluoromethylaniline 16.7 parts by weight of N-hydroxyethyl-N-allyl-2,6-dinitro-4-trifluoromethylaniline is dissolved in 50 parts by weight of benzene. After adding 1 part by weight of dimethylformamide and dripping in 30 parts by weight of thionyl chloride at room temperature the whole is boiled for two hours under reflux. The volatile constituents are distilled off from the reaction mixture at 20 mm Hg, the residue is taken up in ethyl acetate, the solution is washed with ice-water, then with 10% sodium bicarbonate solution and finally again with water and the organic phase is dried over sodium sulfate.

After distilling off the solvent a dark brown oil (95% of theory) is obtained from which, after purifying over silica gel (benzene), yellow crystals may be isolated which have a melting point of 39° to 41° C.

| Analysis: | C | H | N | Cl |
|---|---|---|---|---|
| calc: | 40.7 | 3.1 | 11.9 | 10.0 |
| found: | 40.4 | 3.2 | 11.6 | 9.9 |

Examples of substances prepared in the same way are:

N-chloroethyl-N-cyanoethyl-4-trifluormethyl-2,6-dinitroaniline m.p. 66° to 67° C N,N-bis-chloroethyl-2,6-dinitro-p-toluidine m.p. 66° to 67° C N-propyl-N-cyanoethyl-2,4-dinitro-6-trifluoromethylaniline m.p. 56° C N-allyl-N-cyanomethyl-2,4-dinitro-6-trifluoromethylaniline m.p. 56° C N-n-butyl-N-cyanoethyl-4-trifluoromethyl-2,6-dinitroaniline m.p. 93° C.

The following comparative experiment demonstrates the superiority of the compositions according to this invention over known active ingredients.

EXAMPLE 2

In a greenhouse, loamy sandy soil is filled into pots and then sown with the seeds of cotton (Gossypium sp.), Indian corn (Zea mays), soya beans (Glycine hispida), annual meadow grass (Poa annua), orchard grass (Dactylis glomerata), slender foxtail (Alopecurus myosuroides) and barnyard grass (Panicum cruss-galli). The soil prepared in this manner is treated with 3 kg per hectare of N-allyl-N-β-chloroethyl-4-trifluoromethyl-2,6-dinitroaniline (I), and, for comparison, with 3 kg per hectare of N,N-dipropyl-4-trifluoromethyl-2,6-dinitroaniline (II), these amounts of the active ingredients each being dispersed in 500 liters of water per hectare. After four weeks it is ascertained that compound I, while having the same good herbicidal action as compound II, has superior compatibility with Indian corn and soya beams.

The results of the experiment may be seen from the following table:

|  | Active ingredient | |
|---|---|---|
|  | I | II |
| Crop plants: | | |
| cotton | 0–10 | 0–10 |
| Indian corn | 10–20 | 30–40 |
| soya beans | 10 | 30 |
| Unwanted plants: | | |

-continued

|  | Active ingredient | |
| --- | --- | --- |
|  | I | II |
| annual meadow grass | 100 | 100 |
| orchard grass | 100 | 100 |
| slender foxtail | 90–100 | 90–100 |
| barnyard grass | 90–100 | 90–100 |

0 = no damage
100 = total destruction

The action of the following substances corresponds to that of I:

N-methyl-N-chloroethyl-4-trifluoromethyl-2,6-dinitroaniline

N,N-bis-chloroethyl-4-trifluoromethyl-2,6-dinitroaniline

N-chloroethyl-N-cyanoethyl-4-trifluoromethyl-2,6-dinitroaniline

N-chloroethyl-N-(γ-chloropropyl)-4-trifluoromethyl-2,6-dinitroaniline

N-propyl-N-cyanoethyl-4-trifluoromethyl-2,6-dinitroaniline

N-allyl-N-cyanoethyl-4-trifluoromethyl-2,6-dinitroaniline

N-ethyl-N-cyanoethyl-4-trifluoromethyl-2,6-dinitroaniline

N,N-bis-cyanoethyl-4-trifluoromethyl-2,6-dinitroaniline

N-propyl-N-cyanomethyl-4-trifluoromethyl-2,6-dinitroaniline

N-allyl-N-cyanomethyl-4-trifluoromethyl-2,6-dinitroaniline

N-propyl-N-β-chloroethyl-4-trifluoromethyl-2,6-dinitroaniline

N-isopropyl-N-(γ-chloropropyl)-4-trifluoromethyl-2,6-dinitroaniline.

We claim:

1. 2,6-dinitro-4-trifluoromethyl-N-propyl-N-β-chloroethylaniline.

2. 2,6-dinitro-4-trifluoromethyl-N-allyl-N-β-chloroethylaniline.

* * * * *